(12) United States Patent
Ishibashi et al.

(10) Patent No.: US 9,278,900 B2
(45) Date of Patent: Mar. 8, 2016

(54) METHOD FOR PRODUCING 3,5-DIMETHYLDODECANOIC ACID

(71) Applicant: Shin-Etsu Chemical Co., Ltd., Tokyo (JP)

(72) Inventors: Naoki Ishibashi, Joetsu (JP); Akihiro Baba, Joetsu (JP); Takeshi Kinsho, Joetsu (JP)

(73) Assignee: Shin-Etsu Chemical Co., Ltd. (JP)

( * ) Notice: Subject to any disclaimer, the term of this patent is extended or adjusted under 35 U.S.C. 154(b) by 0 days.

(21) Appl. No.: 14/713,623

(22) Filed: May 15, 2015

(65) Prior Publication Data
US 2015/0344396 A1 Dec. 3, 2015

(30) Foreign Application Priority Data
May 27, 2014 (JP) ................................. 2014-109167

(51) Int. Cl.
*C07C 51/38* (2006.01)
*C07F 3/02* (2006.01)
*C07C 55/02* (2006.01)
*C07C 67/32* (2006.01)
*C07C 67/343* (2006.01)
*C07C 67/347* (2006.01)
*C07C 51/09* (2006.01)

(52) U.S. Cl.
CPC .................. *C07C 51/38* (2013.01); *C07C 51/09* (2013.01); *C07C 55/02* (2013.01); *C07C 67/32* (2013.01); *C07C 67/343* (2013.01); *C07C 67/347* (2013.01); *C07F 3/02* (2013.01)

(58) Field of Classification Search
CPC combination set(s) only.
See application file for complete search history.

(56) References Cited

PUBLICATIONS

Holmbert, Gust.-Ad., et al., The Addition of Grignard Reagents to Alkylidenemalonic Esters, 1969, Acta Chemica Scandinavica, vol. 23, No. 4, pp. 1304-1310.*
Rodstein et al. "Identification and Synthesis of a Female-Produced Sex Pheromone for the Cerambycid Beetle *Prionus californicus*", *J. Chem. Ecol.* 35:590-600 (2009).
Rodstein et al. "Determination of the Relative and Absolute Configurations of the Female-Produced Sex Pheromone of the Cerambycid Beetle *Prionus californicus*", *J. Chem. Ecol.* 37:114-124 (2011).
Petrow et al. "Synthese und oberflächenaktive Eigenschaften der verzweigten Säuren der Reihe $C_nH_{2n+1}COOH$ der Zusammensetzung $C_{10}$—$C_{20}$", *Fette, Seifen, Anstrichmittel* 61:940-946 (1959).
Nikishin et al., "Synthesis and Properties of Branched Acids of CnH2n+1 Series with C12-C20 Composition. II," Zhurnal Obshchei Khimii, vol. 30, 1960, pp. 3543-3548; Retrieved from Database Caplus, Chemical Abstracts Service, Columbus, OH, USA, Apr. 22, 2001, 2 pages.
European Search Report, European Application No. 15168198.8, Oct. 16, 2015, 5 pages.

\* cited by examiner

*Primary Examiner* — Yate K Cutliff
(74) *Attorney, Agent, or Firm* — Myers Bigel Sibley & Sajovec

(57) ABSTRACT

Provided is a process for producing 3,5-dimethyldodecanoic acid, which is an active ingredient of the pheromone of California prionus. More specifically provided is a method for producing 3,5-dimethyldodecanoic acid (5) comprising the steps of converting 2-methylnonyl halide (1) to a 2-methylnonyl metal reagent (2), and reacting the 2-methylnonyl metal reagent (2) with 2-ethylidene malonic acid ester (3) to form 2-(1,3-dimethyldecyl)malonic acid ester (4) as a result of 1,4-addition of the 2-methylnonyl metal reagent (2) to the 2-ethylidene malonic acid ester (3), as shown in the following scheme:

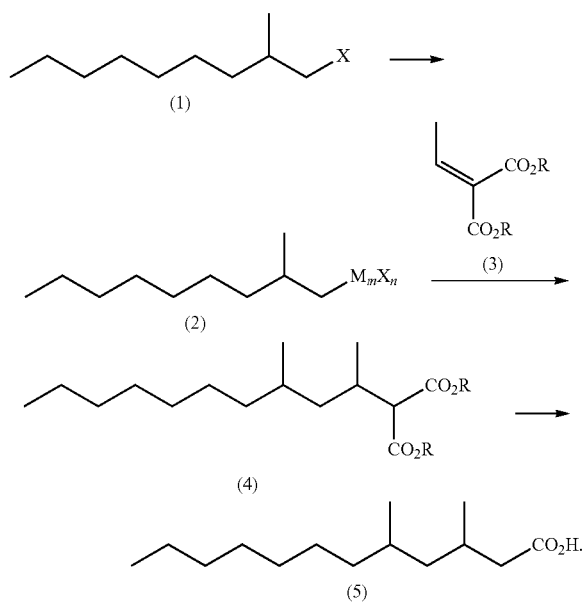

3 Claims, No Drawings

METHOD FOR PRODUCING 3,5-DIMETHYLDODECANOIC ACID

RELATED APPLICATION

This application claims priority from Japanese Patent Application No, 2014-109167, filed May 27, 2014, the disclosure of which is incorporated by reference herein in its entirety.

FIELD AND BACKGROUND OF THE INVENTION

The present invention relates to a method for producing 3,5-dimethyldodecanoic acid which is a sex pheromone of California prionus (*Prionus californicus*).

Sex pheromones of insects are usually bioactive substances released by individual females and having a function of attracting individual males. They show high attracting activity even in small amounts. Sex pheromones are widely used as a means for predicting the outbreak of insects or finding geological diffusion thereof (emergence into specific areas) or as a means for pest control. As a means for pest control, control methods called "mass trapping", "lure & kill or attract & kill", "lure & infect or attract & infect", or "mating disruption" have been widely carried out in practice. To utilize a sex pheromone, economical production of a required amount of an active ingredient of the pheromone is necessary for basic research and further for a practical application.

California prionus (*Prionus californicus*), one of long horn beetles, has a wide distribution in Northwestern America. It is an insect pest to various kinds of perennial plants. Among them, damage by this insect pest to hops has been a serious problem. This insect pest has a life cycle as long as 3 to 5 years but it spends most of its life as a larva in soil, more specifically, in the roots or trunks of plants such as hop to be damaged by the insect pest so that it cannot be controlled easily by agrichemicals.

Millar et al. have revealed that as a result of syntheses of candidate compounds presumed from the mass spectra of an extract from this insect pest, the sex pheromone of the insect pest is 3,5-dimethyldodecanoic acid (J. Chem. Ecol., 2009, 35, 590-600). Also in this journal article, Millar et al. synthesize this product by bromination of 2-methyl-1-nonanol, subsequent conversion into a corresponding Grignard reagent, and then reaction with β-butyrolactone.

Further, Petrov et al. synthesize 3,5-dimethyldodecanoic acid by coupling between heptyl magnesium bromide and 2-chloro-3-pentene, addition of hydrogen bromide, alkylation of ethyl malonate, hydrolysis of the resulting ester, and decarboxylation (Fette, Seifen, Anstrichmittel, 1959, 61, 940-946).

Still further, Millar et al. stereoselectively synthesize a (3R,5S)-form and a (3S,5R)-form of 3,5-dimethyldodecanoic acid by asymmetric 1,4-addition of methyl magnesium bromide to 2-decenoate ester, reduction of the ester, a Wittig reaction, asymmetric 1,4-addition again of methyl magnesium bromide to the unsaturated ester thus obtained, and finally hydrolysis of the ester (J. Chem. Ecol., 2011, 37, 114-124).

SUMMARY OF THE INVENTION

The method described in J. Chem. Ecol., 2009, 35, 590-600 is far from an industrial synthesis method. It is because β-butyrolactone to be used in the reaction is very expensive and not easily available industrially, and 3,5-dimethyldodecanoic acid obtained by this method cannot be purified by distillation so that silica gel flash chromatography is used for separation or purification.

The method described in Fette, Seifen, Anstrichmittel, 1959, 61, 940-946 is also far from an industrial synthesis method. It is because an alkylation yield of ethyl malonate is 32%, which is very low, and addition of hydrogen bromide is carried out under severe conditions requiring hydrogen bromide in gas form.

In the method described in J. Chem. Ecol., 2011, 37, 114-124, the number of steps necessary for synthesis of 3,5-dimethyldodecanoic acid from 2-decenoic acid is even six and the product yields of asymmetric 1,4-addition conducted twice are as low as 53% and 12%, respectively. A yield of another step is also low so that a total yield from 2-decenoic acid is only 1.7%. From a standpoint of use of silica gel flash chromatography for separating or purifying an intermediate in each step, this method is far from an industrial synthesis method. In addition, 3,5-dimethyldodecanoic acid is obtained only as a crude product and this journal article does not include a purification method thereof.

Thus, when the conventional production methods are used, it is considered to be very difficult to industrially produce a sufficient amount of 3,5-dimethyldodecanoic acid because of various reasons such as yield and isolation or purification of an intermediate or the intended product.

With the foregoing in view, the invention has been made. An object of the invention is to provide a short process for simply and efficiently producing 3,5-dimethyldodecanoic acid, which is an active ingredient of the pheromone of California prionus, for supplying an adequate amount of the active ingredient necessary for biological or agricultural active tests, practical applications and use.

The present inventors have proceeded with an extensive investigation in order to achieve the above-described object. As a result, it has been found that 2-methylnonyl halide (1) is converted to a 2-methylnonyl metal reagent (2); 1,4-addition of the 2-methylnonyl metal reagent (2) to 2-ethylidene malonic acid ester (3) can efficiently produce 2-(1,3-dimethyldecyl)malonic acid ester (4); and conversion of the resulting 2-(1,3-dimethyldecyl)malonic acid ester (4) into 3,5-dimethyldodecanoic acid (5) enables industrial production of 3,5-dimethyldodecanoic acid only by isolation and purification through distillation. Thus, the invention has been completed.

A method for producing 3,5-dimethyldodecanoic acid comprising the steps of:

converting 2-methylnonyl halide (1):

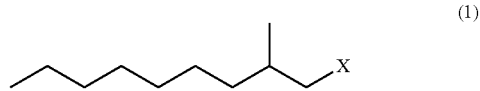

wherein X represents a halogen atom,
to a 2-methylnonyl metal reagent (2):

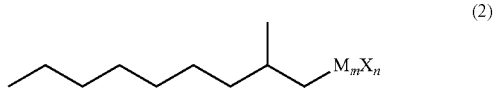

wherein M represents a monovalent or divalent metal, m stands for 1 or 0.5, and when m stands for 1, n stands for 0 or 1, and when m stands for 0.5, n stands for 0, reacting the 2-methylnonyl metal reagent (2) with 2-ethylidene malonic acid ester (3):

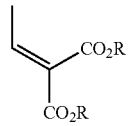
(3)

wherein Rs may be the same or different and each represents a monovalent hydrocarbon group having from 1 to 5 carbon atoms, to form 2-(1,3-dimethyldecyl)malonic acid ester (4):

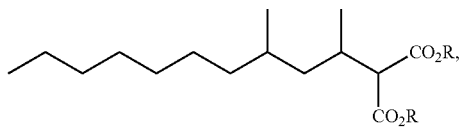
(4)

as a result of 1,4-addition of the 2-methylnonyl metal reagent (2) to the 2-ethylidene malonic acid ester (3), and subjecting the 2-(1,3-dimethyldecyl)malonic acid ester (4) to decarboxylation or dealkoxycarbonylation reaction to obtain 3,5-dimethyldodecanoic acid (5):

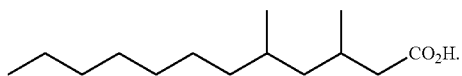
(5)

According to the invention, an 1,4-adduct can be obtained in a high yield while suppressing formation of by-products. The 2-methylnonyl halide and the 2-ethylidene malonic acid ester, which are raw materials in the invention, are available at low cost. From these inexpensive raw materials, 3,5-dimethyldodecanoic acid can be obtained efficiently with fewer steps. Further, the industrial production method of 3,5-dimethyldodecanoic acid is provided, requiring only distillation for isolation and purification.

DETAILED DESCRIPTION OF THE PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

According to the invention, one of the starting materials is 2-methylnonyl halide (1) represented by the following formula. In the formula, X represents a halogen atom, preferably a chlorine atom, a bromine atom or an iodine atom.

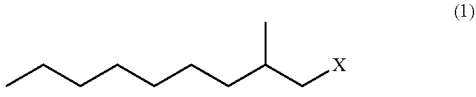
(1)

The 2-methylnonyl halide (1) is commercially available or can be obtained by the existing method, for example, a method described in J. Chem. Ecol., 2002, 28, 1237-1254 or Bulletin de la Societe Chimique de France, 1991, 397-406.

The 2-methylnonyl halide (1) is converted to 2-methylnonyl metal reagent (2) represented by the formula below. In the formula, M represents a monovalent or divalent metal, preferably a monovalent alkali metal, monovalent copper or a divalent metal, more preferably a metal atom selected from the group consisting of lithium, sodium, magnesium, zinc, cadmium and copper. X has the same meaning as described above. When m is 1, n stands for 0 or 1, and when m is 0.5, n stands for 0.

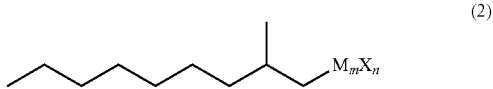
(2)

When M contained by the metal reagent is an alkali metal such as lithium or sodium, m stands for 1 and n stands for 0. Examples of the corresponding metal reagent include 2-methylnonyl lithium and 2-methylnonyl sodium.

When M contained by the metal reagent is a divalent metal such as magnesium, zinc or cadmium, m stands for 1 or 0.5 and n stands for 1 or 0. Examples of the corresponding metal reagent having 1 as m include 2-methylnonylmagnesium chloride, 2-methylnonylmagnesium bromide, 2-methylnonylmagnesium iodide, 2-methylnonylzinc bromide and 2-methylnonylcadmium iodide. Examples of the metal reagents having 0.5 as m include dialkyl metal reagents such as bis(2-methylnonyemagnesium and bis(2-methylnonyl) zinc.

When M is a monovalent copper, m stands for 1 and n stands for 0. Examples of the corresponding metal reagent include 2-methylnonylcopper. When M is a 1:1 (molar ratio) combination of monovalent copper and monovalent alkali metal, m stands for 0.5 and n stands for 0. Examples of the corresponding metal reagent include ate complexes such as bis(2-methylnonyl) copper lithium.

Examples of the method for converting the 2-methylnonyl halide (1) to the 2-methylnonyl metal reagent (2) include a direct reaction between the 2-methylnonyl halide (1) and a single metal, and a halogen-metal exchange reaction between the 2-methylnonyl halide (1) and another organic metal reagent. It is also possible to subject a portion or all of the 2-methylnonyl metal reagent once produced to transmetalation for formation of a 2-methylnonyl metal reagent (2) as a result of exchange of metal element.

The direct reaction between the 2-methylnonyl halide and a single metal includes, for example, a reaction for producing 2-methylnonylmagnesium chloride from 2-methylnonyl chloride and metal magnesium.

The halogen-metal exchange reaction between the 2-methylnonyl halide and another organic metal reagent includes, for example, a reaction for producing 2-methylnonyllithium from 2-methylnonyl bromide and tert-butyl lithium.

The method of subjecting a portion or all of the 2-methylnonyl metal reagent to transmetalation for formation of a 2-methylnonyl metal reagent (2) as a result of exchange of metal element includes, for example, a reaction for producing 2-methylnonylcopper from 2-methylnonyllithium and copper iodide.

The solvent to be used for producing the 2-methylnonyl metal reagent (2) is not particularly limited insofar as it is unreactive to the 2-methylnonyl metal reagent (2). Preferable examples of the solvent include hydrocarbons such as hexane, heptane, benzene, toluene, xylene and cumene; and ethers such as diethyl ether, dibutyl ether, tetrahydrofuran and 1,4-dioxane. The solvent may be used alone or in a mixture of two or more. The amount of the solvent to be used for the production of the 2-methylnonyl metal reagent (2) is preferably from 10 g to 10,000 g relative to 1.00 mol of the 2-methylnonyl metal reagent (2).

The reaction temperature for the production of the 2-methylnonyl metal reagent (2) varies depending on the kind of the metal element or production method of the metal reagent. It may be from −78° C. to 120° C., preferably from −50° C. to 100° C., more preferably from −30° C. to 80° C.

The reaction time for the production of the 2-methylnonyl metal reagent (2) can be selected freely. The reaction time is desired from a standpoint of yield to be a period of time for completing the reaction while monitoring the reaction by gas chromatography (GC) or silica gel thin-layer chromatography (TLC). The reaction time is typically from about 0.5 to 24 hours.

The 2-ethylidene malonic acid ester (3), which is the other starting material, is represented by the formula below, in which Rs may be the same or different and each represents a hydrocarbon group having from 1 to 5 carbon atom. The Rs are preferably the same from a standpoint of producibility and cost of the 2-ethylidene malonic acid ester (3).

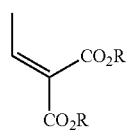

(3)

The R independently represents a monovalent hydrocarbon group having from 1 to 5 carbon atoms, preferably from 1 to 3 carbon atoms. Examples of the monovalent hydrocarbon group include linear or branched saturated hydrocarbon groups such as methyl, ethyl, n-propyl, n-butyl, n-pentyl and isopropyl; linear or branched unsaturated hydrocarbon groups such as vinyl, 1-propenyl, 2-propenyl, 2-methyl-1-propenyl, ethynyl, propynyl and 1-butynyl groups; and hydrocarbon groups having an isomeric relationship therewith. One or more hydrogen atoms of the hydrocarbon group may be replaced by a methyl group, an ethyl group or the like. Among them, a highly reactive lower alkyl group or primary hydrocarbon group is preferred from a standpoint of reactivity in subsequent reactions and availability. Taking the above into consideration, particularly preferred examples of R include methyl, ethyl and n-propyl groups.

The 2-ethylidene malonic acid ester (3) is commercially available and can be produced by existing methods such as those described in Synthesis, 6, 1045-1049 (2006) and Organic Syntheses, Coll. Vol. 4, 293-294 (1963).

Next, the step of reacting the 2-methylnonyl metal reagent (2) obtained by the above method with the 2-ethylidene malonic acid ester (3) to produce a 2-(1,3-dimethyldecyl)malonic acid ester (4) as a result of 1,4-addition of the 2-methylnonyl metal reagent (2) to the 2-ethylidene malonic acid ester (3), as shown in the following scheme. In the scheme, M and R have the same meanings as described above.

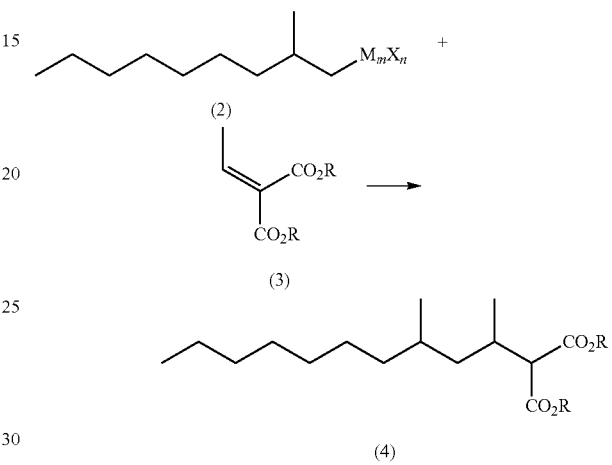

It is usually expected that 3,5-dimethyldodecanoic acid can be obtained more easily by the route of 1,4-addition of the 2-methylnonyl metal reagent (2) to crotonic acid ester, followed by hydrolysis of the ester than the route by way of production of 2-(1,3-dimethyldecyl)malonic acid ester (4). In practice, however, the 1,4-addition of the 2-methylnonyl metal reagent to crotonic acid ester leads to formation of by-products so that a 3,5-dimethyldodecanoic acid ester can be obtained only in a low yield. For example, an enolate formed by the first 1,4-addition the 2-methylnonyl metal reagent to crotonic acid ester is further subjected to 1,4-addition to crotonic acid ester to form a by-product. Thus, the by-products result from repeated 1,4-addition to the crotonic acid ester.

On the other hand, according to the invention, 1,4-addition of the 2-methylnonyl metal reagent (2) to the 2-ethylidene malonic acid ester (3) is superior in that the 1,4-adduct (4) can be obtained in a good yield. This good yield is attributable to, for example, that negative charge of the enolate formed by the addition reaction is stabilized by two ester carbonyl groups so that further reaction is suppressed.

The amount of the 2-methylnonyl metal reagent (2) to be used in the 1,4-addition reaction is preferably from 0.80 to 1.50 mol, more preferably from 0.90 to 1.20 mol, relative to 1.00 mol of the 2-ethylidene malonic acid ester (3). When the amount is less than 0.80 mol, the 2-ethylidene malonic acid ester remains unreacted, leading to deterioration in cost effectiveness. When the amount is more than 1.50 mol, the excess amount of the metal reagent may cause a side reaction with an ester portion or may remain unreacted, leading to deterioration in cost effectiveness.

The 1,4-addition proceeds in the absence of a transition metal salt but it is preferably carried out in the presence of a transition metal salt from a standpoint of yield. Examples of the transition metal salt include a salt of copper, zinc, nickel, palladium or iron. The transition metal salt may be used alone or in a mixture of two or more. A copper salt is particularly preferred from a standpoint of yield and cost. Examples of the copper salt include copper halide such as cuprous chloride, cupric chloride, cuprous bromide, cupric bromide, cuprous iodide and cupric iodide; cuprous acetate; cupric acetate; and cuprous cyanide. The copper halide is particularly preferred from a standpoint of yield.

The amount of the transition metal salt is preferably from 0.0001 mol to 1.00 mol, more preferably from 0.0005 mol to 0.20 mol, more preferably from 0.001 mol to 0.10 mol, each relative to 1.00 mol of the 2-ethylidene malonic acid ester (3).

The 1,4-addition reaction may be carried out while adding a Lewis acid or a Lewis base together with the transition metal salt. Examples of the Lewis acid include halide salts such as lithium chloride, lithium bromide, lithium iodide, magnesium chloride, magnesium bromide, magnesium iodide and aluminum chloride; boron compounds such as boron trifluoride-diethyl ether complexes; and halogenated silicon compounds such as chlorotrimethylsilane, bromotrimethylsilane and iodotrimethylsilane. The Lewis acid may be used alone or in a mixture of two or more. Examples of the Lewis base include phosphor compounds such as triethyl phosphite, triphenylphosphine and hexamethylphosphoric triamide (HMPA); nitrogen compounds such as dimethylimidazolidinone and tetramethylethylene diamine; and sulfur compounds such as dimethylsulfide. The Lewis base may be used alone or in a mixture of two or more.

The amount of the Lewis acid or Lewis base to be used in the 1,4-addition reaction is preferably from 0.0001 mol to 100 mol, more preferably from 0.001 mol to 10.0 mol, each relative to 1.00 mol of the 2-ethylidene malonic acid ester (3).

Although the solvent for the 1,4-addition reaction is not particularly limited insofar as the solvent is unreactive toward the 2-methylnonyl metal reagent (2). Preferable examples of the solvent include hydrocarbons such as hexane, heptane, benzene, toluene, xylene and cumene; and ethers such as diethyl ether, dibutyl ether, tetrahydrofuran and 1,4-dioxane. The solvent may be used alone or in a mixture of two or more. The amount of the solvent to be used for the 1,4-addition reaction is preferably from 10 g to 10,000 g, relative to 1.00 mol of the 2-methylnonyl metal reagent (2).

The reaction temperature of the 1,4-addition reaction is preferably from −78° C. to 50° C., more preferably −50° C. to 40° C., still more preferably from −30° C. to 30° C. When the reaction temperature is less than −78° C., the reaction may not proceed smoothly. When the reaction temperature is more than 50° C., side reactions may increase.

The reaction time of the 1,4-addition reaction can be selected freely. The reaction time is desired from a standpoint of yield to be a period of time for completing the reaction while monitoring the reaction by gas chromatography (GC) or silica gel thin-layer chromatography (TLC). It is usually from about 0.5 to 24 hours. Isolation and purification for obtaining an intended 2-(1,3-dimethyldecyl)malonic acid ester may be carried out by an method appropriately selected from purification methods in usual organic syntheses, such as distillation under reduced pressure and a various type of chromatography. The distillation under reduced pressure is preferred from a standpoint of industrial economy. When the intended product has a sufficient purity, the crude product can be provided for the subsequent step as it is.

Next, the step of subjecting the 2-(1,3-dimethyldecyl)malonic acid ester (4) to decarboxylation or dealkoxycarbonylation to obtain 3,5-dimethyldodecanoic acid (5) as shown in the following scheme will be described. In the scheme, the Rs may be the same or different and each represents a monovalent hydrocarbon group having from 1 to 5 carbon atoms.

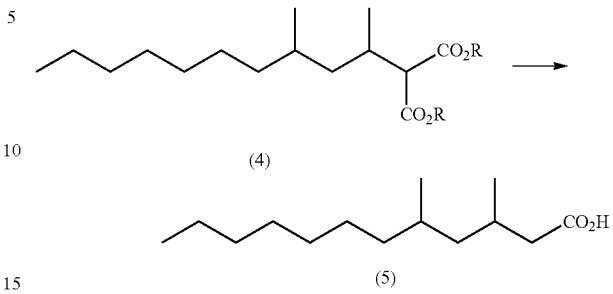

This step may preferably comprises hydrolyzing the 2-(1,3-dimethyldecyl)malonic acid ester (4) into 2-(1,3-dimethyldecyl)malonic acid (6) and subjecting the 2-(1,3-dimethyldecyl)malonic acid (6) to decarboxylation to obtain the 3,5-dimethyldodecanoic acid (5) as shown in the following scheme.

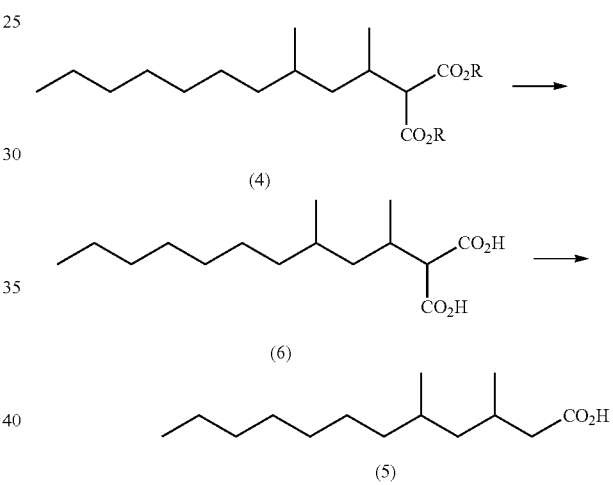

Hydrolysis reaction of the ester is preferably carried out typically using an aqueous solution of an acid or a base in the presence of an organic solvent or in the absence of an organic solvent with optional cooling or heating.

Examples of the acid to be used for the hydrolysis reaction of the ester include mineral acids such as hydrochloric acid, hydrobromic acid, sulfuric acid and nitric acid; and organic acids such as acetic acid, oxalic acid, trifluoroacetic acid, methanesulfonic acid, benzenesulfonic acid and p-toluenesulfonic acid. The acid may be used alone or in a mixture of two or more. The acid can be selected appropriately in consideration of the kind or reactivity of the substrate. The acid is particularly preferably hydrochloric acid or sulfuric acid from a standpoint of reactivity and cost. The amount of the acid differs depending on the kind of the substrate or the acid. It is preferably from 0.001 mol to 100 mol, more preferably from 0.01 mol to 10 mol, each relative to 1.00 mol of the substrate.

Examples of the base to be used for the hydrolysis reaction of the ester include carbonates such as sodium carbonate and potassium carbonate; hydroxide salts such as potassium hydroxide, sodium hydroxide and lithium hydroxide; and organic bases such as triethylamine, diisopropylethylamine, tributylamine, pyrrolidine, piperidine, morpholine and piperazine. The base may be used alone or in a mixture of two or more. The base can be selected appropriately in consideration of the kind or reactivity of the substrate. The base is particularly preferably a hydroxide salt from a standpoint of the reactivity and cost. The amount of the base differs depending on the kind of the substrate or base. It is preferably from 2.00 mol to 10.0 mol, more preferably from 2.20 mol to 5.00 mol, each relative to 1.00 mol of the substrate.

When the hydrolysis of the ester is carried out under basic conditions, the salt of 2-(1,3-dimethyldecyl)malonic acid has to be converted into free 2-(1,3-dimethyldecyl)malonic acid by addition of an acid before decarboxylation. Examples of the acid to be used therefor include mineral acids such as hydrochloric acid, hydrobromic acid, sulfuric acid and nitric acid; and organic acids such as acetic acid, oxalic acid, trifluoroacetic acid, methanesulfonic acid, benzenesulfonic acid and p-toluenesulfonic acid. The acid may be used alone or in a mixture of two or more. The acid can be selected appropriately in consideration of the kind or reactivity of the substrate. The acid is particularly preferably hydrochloric acid or sulfuric acid from a standpoint of reactivity and cost. The amount of the acid to be added should be equal to or greater than an amount required for converting the salt of 2-(1,3-dimethyldecyl)malonic acid into free 2-(1,3-dimethyldecyl)malonic acid.

Examples of the solvent in the hydrolysis reaction of the ester include water, ethers such as diethyl ether, dibutyl ether, tetrahydrofuran and 1,4-dioxane; hydrocarbons such as hexane, heptane, benzene, toluene, xylene and cumene; aprotic polar solvents such as N,N-dimethylformamide (DMF), 1,3-dimethyl-2-imidazolidinone (DMI), dimethylsulfoxide (DMSO) and hexamethylphosphoric triamide (HMPA); and nitriles such as acetonitrile and propionitrile. The solvent may be used alone or in a mixture of two or more. The solvent should be unreactive to the acid or base used in the hydrolysis reaction. The solvent to be used in the hydrolysis reaction of the ester is preferably from 10 g to 10,000 g, relative to 1.00 mol of the 2-(1,3-dimethyldecyl)malonic acid ester (4).

When decarboxylation is carried out without removal of an alcohol (ROH) generated during the hydrolysis reaction of the ester, re-esterification inevitably proceeds so that the alcohol is preferably removed by distillation or extraction during or after the hydrolysis of the ester.

The reaction temperature of the hydrolysis of the ester can be selected in consideration of the kind of the substrate or the acid or base to be used for the reaction. The reaction temperature is preferably from 0° C. to 250° C., more preferably from 20° C. to 200° C. The reaction time can be selected freely. The reaction time is desired from a standpoint of yield to be a period of time for completing the reaction while monitoring the reaction by gas chromatography (GC) or silica gel thin-layer chromatography (TLC). The reaction time is usually from about 0.5 to 24 hours.

Next, the decarboxylation for converting 2-(1,3-dimethyldecyl)malonic acid (6) to 3,5-dimethyldodecanoic acid (5) will be described.

The decarboxylation can be carried out by heating the 2-(1,3-dimethyldecyl)malonic acid (6) in the presence of a solvent or in the absence of a solvent.

The decarboxylation can also be carried out by heating the reaction mixture of the 2-(1,3-dimethyldecyl)malonic acid (6) obtained by the hydrolysis of the ester as it is. Alternatively, the decarboxylation can be carried out after isolation of the 2-(1,3-dimethyldecyl)malonic acid (6) through separation operation or the like. The decarboxylation after isolation of the 2-(1,3-dimethyldecyl)malonic acid (6) can shorten the reaction time because the reaction temperature of decarboxylation can be increased.

When the ester is hydrolyzed under acidic conditions, hydrolysis of the ester and decarboxylation may be carried out simultaneously. In this case, in order to prevent above-mentioned re-esterification, the reaction is carried out preferably while removing the alcohol (ROH).

Examples of the solvent to be used in the decarboxylation include ethers such as diethyl ether, dibutyl ether, tetrahydrofuran and 1,4-dioxane; hydrocarbons such as hexane, heptane, benzene, toluene, xylene and cumene; aprotic polar solvents such as N,N-dimethylformamide (DMF), 1,3-dimethyl-2-imidazolidinone (DMI), dimethylsulfoxide (DMSO) and hexamethylphosphoric triamide (HMPA); and nitriles such as acetonitrile and propionitrile; and water. The solvent may be used alone or in a mixture of two or more. The solvent to be used in the decarboxylation is preferably from 0 g to 10,000 g, relative to 1.00 mol of the 2-(1,3-dimethyldecyl)malonic acid (6).

The reaction temperature in the decarboxylation can be selected in consideration of the acid and/or solvent to be used for the reaction. The reaction temperature is preferably from 60° C. to 250° C., more preferably from 80° C. to 200° C. The reaction time can be selected freely. The reaction time may be preferably a period of time for allowing the reaction to proceed fully by monitoring the reaction by thin-layer chromatography (TLC). The reaction time is usually preferably from 0.5 to 48 hours.

The step of converting the 2-(1,3-dimethyldecyl)malonic acid ester (4) to 3,5-dimethyldodecanoic acid (5) may comprise subjecting the 2-(1,3-dimethyldecyl)malonic acid ester (4) to dealkoxycarbonylation in the presence of a Lewis acid to form 3,5-dimethyldodecanoic acid ester (7) and hydrolyzing the 3,5-dimethyldodecanoic acid ester (7) into 3,5-dimethyldodecanoic acid (5), as shown in the following scheme.

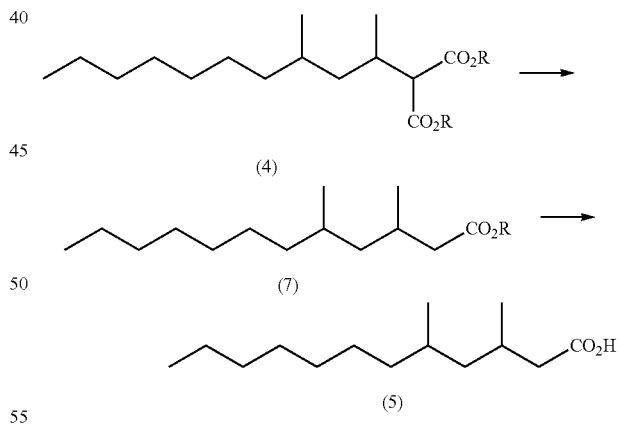

Examples of the Lewis acid to be used for the dealkoxycarbonylation include halide salts such as lithium chloride, sodium chloride, potassium chloride, lithium bromide, sodium bromide, potassium bromide, lithium iodide, sodium iodide and potassium iodide. The Lewis acid may be used alone or in a mixture of two or more. The Lewis acid can be selected appropriately in consideration of the kind or reactivity of the substrate. The Lewis acid is particularly preferably sodium chloride from a standpoint of reactivity and cost. The amount of the Lewis acid to be used for the dealkoxycarbonylation differs depending on the kind of the substrate. It is preferably from 0.80 mol to 100 mol, more preferably from 1.00 mol to 10.0 mol, each relative to 1.00 mol.

Examples of the solvent to be used for dealkoxycarbonylation include alcohols such as methanol, ethanol, isopropyl alcohol, t-butyl alcohol, benzyl alcohol, methoxyethanol, ethoxyethanol, diethylene glycol monomethyl ether and triethylene glycol monomethyl ether; ethers such as diethyl ether, dibutyl ether, tetrahydrofuran and 1,4-dioxane; hydrocarbons such as hexane, heptane, benzene, toluene, xylene and cumene; aprotic polar solvents such as N,N-dimethylformamide (DMF), 1,3-dimethyl-2-imidazolidinone (DMI), dimethylsulfoxide (DMSO) and hexamethylphosphoric triamide (HMPA); nitriles such as acetonitrile and propionitrile; and water. The solvent may be used alone or in a mixture of two or more. The solvent is particularly preferably a combination of DMSO and water from a standpoint of solubility or boiling point of the Lewis acid. The amount of the solvent to be used in dealkoxycarbonylation is preferably from 0 g to 10,000 g, relative to 1.00 mol of the 2-(1,3-dimethyldecyl) malonic acid ester (4).

The reaction temperature in the dealkoxycarbonylation can be selected in consideration of the kind or reactivity of the substrate or the kind of the Lewis acid to be used. The reaction temperature is preferably from 50° C. to 250° C., more preferably from 100° C. to 200° C. The reaction time can be selected freely. The reaction time may be a period of time for allowing the reaction to proceed fully by monitoring the progress of the reaction by thin-layer chromatography (TLC). The reaction time is usually preferably from 0.5 to 24 hours.

The 3,5-dimethyldodecanoic acid ester (7) obtained by dealkoxycarbonylation in the presence of a Lewis acid is hydrolyzed into 3,5-dimethyldodecanoic acid (5). The hydrolysis is carried out in the same manner as for the above-mentioned hydrolysis of the 2-(1,3-dimethyldecyl)malonic acid ester (4) except that the amount of the base used for the reaction is preferably from 1.00 mol to 10.0 mol, more preferably from 1.10 mol to 5.00 mol each relative to 1.00 mol of the 3,5-dimethyldodecanoic acid ester (7).

As mentioned above, the method for simply and efficiently producing 3,5-dimethyldodecanoic acid, which is an active ingredient of the pheromone of California prionus, can be provided to supply an adequate amount of the active ingredient required for applications or use.

Hereafter, specific embodiments of the present invention will be described in detail by way of examples. However, it should not be construed that the present invention is limited to those examples.

EXAMPLES

Example 1-1

Production of ethyl 2-(1,3-dimethyldecyl)malonate (4Et)

(Example in which Each of Two Rs Represents an Ethyl Group)

In a nitrogen atmosphere, magnesium (3.17 g, 0.131 mol) and tetrahydrofuran (37 g) were placed in a reaction vessel and stirred at from 60 to 65° C. for 30 minutes. Then, 2-methylnonyl chloride (1Cl) (21.9 g, 0.124 mol) was added dropwise thereto, and stirred at from 70 to 75° C. for 2 hours to produce 2-methylnonyl magnesium chloride (2MgCl).

In a nitrogen atmosphere, cuprous chloride (0.30 g, 0.0030 mol), tetrahydrofuran (68 g) and triethyl phosphite (0.90 g, 0.0078 mol) were placed in another reactor, and then cooled to −10° C. to 0° C. with stirring. Then, a solution of ethyl 2-ethylidene malonate (3Et) (22.0 g, 0.118 mol) in tetrahydrofuran (68 g) was added thereto, and then the above produced 2-methylnonylmagnesium chloride solution was added dropwise thereto at −10° C. to 0° C. The reaction mixture was stirred at Q to 10° C. for one hour. A mixture of ammonium chloride (6.5 g), 20% by weight hydrochloric acid (22 g) and water (90 g) was added to the reaction mixture to terminate the reaction. The organic phase was washed with an aqueous saturated sodium chloride solution, dried over magnesium sulfate, and concentrated under reduced pressure to obtain a crude product (42.1 g, 0.0909 mol) of ethyl 2-(1, 3-dimethyldecyl) malonate (4Et). The yield was 73%. The resulting crude product was provided for the subsequent reaction. However, a sample for analysis was obtained by distillation under reduced pressure (bp: from 150 to 155° C./2 mmHg).

IR (D-ATR): ν=2958, 2926, 2855, 1755, 1734, 1464, 1369, 1302, 1234, 1175, 1150, 1096, 1034 cm$^{-1}$.

$^1$H-NMR (500 MHz, CDCl$_3$): δ=0.84-0.88 (6H, m), 0.94 (1.5H, d, J=6.9 Hz), 0.97 (1.5H, d, J=6.9 Hz), 0.99-1.52 (21H, m), 2.27-2.36 (21H, m), 3.16 (0.5H, d, J=8.0 Hz), 3.21 (0.5H, d, J=7.7 Hz), 4.13-4.23 (4H, m) ppm.

$^{13}$C-NMR (125 MHz, CDCl$_3$): δ=14.08, 14.10, 16.77, 17.34, 18.85, 20.46, 22.65, 26.72, 27.02, 29.32, 29.36, 29.84, 29.91, 29.98, 30.00, 31.04, 31.86, 31.88, 35.78, 38.09, 41.75, 42.20, 57.60, 58.56, 60.98, 61.07, 168.80, 169.04 ppm.

Example 1-2

Production of methyl 2-(1,3-dimethyldecyl)malonate (4Me)

(Example in which Each of Two Rs Represents a Methyl Group)

In the same manner as in Example 1-1 except that methyl 2-ethylidene malonate (3Me) (18.7 g, 0.118 mol) was used in the place of ethyl 2-ethylidene malonate (3Et) (22.0 g, 0.118 mol), a crude product (43.4 g, 0.0859 mol) of methyl 2-(1,3-dimethyldecyl)malonate (4Me) was obtained. The yield was 69%.

Example 1-3

Production of ethyl 2-(1,3-dimethyldecyl)malonate (4Me)

(Room Temperature Reaction, and Dropwise Addition of Ethylidene Malonate to Grignard reagent).

In a nitrogen atmosphere, magnesium (3.52 g, 0.145 mol) and tetrahydrofuran (41 g) were placed in a reaction vessel and stirred at from 60 to 65° C. for 30 minutes. Then, 2-methylnonyl chloride (1 Cl) (24.4 g, 0.138 mol) was added dropwise thereto, and stirred at from 70 to 75° C. for 2 hours to produce 2-methylnonylmagnesium chloride (2MgCl).

The above reaction mixture was cooled to 20° C. and subjected to addition of cuprous chloride (0.34 g, 0.0035 mol), tetrahydrofuran (127 g) and triethyl phosphite (1.00 g, 0.0086 mol). Then, a solution of ethyl 2-ethylidene malonate (3Et) (24.4 g, 0.131 mol) in tetrahydrofuran (25 g) was added dropwise thereto at from 20° to 30° C. and the resulting mixture was stirred at from 20° C. to 30° C. for one hour. A mixture of ammonium chloride (6.5 g), 20% by weight hydrochloric acid (22 g) and water (90 g) was added to the reaction mixture to terminate the reaction. The organic phase was washed with an aqueous saturated sodium chloride solution, dried over magnesium sulfate, and concentrated under reduced pressure to obtain a crude product (47.70 g, 0.105 mol) of ethyl 2-(1,3-dimethyldecyl) malonate (4Et). The yield was 76%.

Comparative Example 1

1,4-Addition to Crotonic Acid Ester

In a nitrogen atmosphere, magnesium (2.86 g, 0.118 mol) and tetrahydrofuran (35 g) were placed in a reaction vessel and stirred at from 60° C. to 65° C. for 30 minutes. Then, 2-methylnonyl chloride (1Cl) (18.1 g, 0.103 mol) was added dropwise thereto and the reaction mixture was stirred at from 70° to 75° C. for 2 hours to produce 2-methylnonyl magnesium chloride (2MgCl).

The above reaction mixture was cooled to −10° C., and subjected to addition of cuprous chloride (0.07 g, 0.001 mol) and tetrahydrofuran (31 g). Then, a solution of t-butyl crotonate (16.1 g, 0.113 mol) in tetrahydrofuran (31 g) was added dropwise thereto at from −10° C. to 0° C. During the dropwise addition, cuprous chloride (0.07 g, 0.001 mol) was added twice. After completion of the dropwise addition, the reaction mixture was stirred at from 0° C. to 10° C. for one hour. Acetic acid (9 g) was added to the reaction mixture to terminate the reaction. A mixture of ammonium chloride (1 g), 20% by weight hydrochloric acid (1.5 g) and water (27 g) was added thereto. Then, the organic phase was washed with an aqueous saturated sodium chloride solution, dried over magnesium sulfate, and concentrated under reduced pressure to obtain a crude product (31.8 g, 0.0246 mol) of t-butyl 3,5-dimethyldodecanoate. The yield was 24%. As described above, the yield became low because of by-products including the by-product formed by the 1,4-addition of an enolate, which has been formed by the first 1,4-addition, to t-butyl crotonate.

Example 2-1

Production of 3,5-dimethyldodecanoic acid (5)

(Hydrolysis in the Presence of Base, Followed by Isolation of Dicarboxylic Acid, and Subsequent Decarboxylation)

In a nitrogen atmosphere, the crude product (41.6 g, 0.0899 mol) of ethyl 2-(1,3-dimethyldecyl)malonate (4Et) obtained in the method of Example 1-1 and a 13% by weight aqueous sodium hydroxide solution (87 g) were placed in a reaction vessel and stirred for one hour under refluxing with heating. Then ethanol thus generated therein was distilled off in one hour. The resulting mixture was subjected to addition of 20% by weight hydrochloric acid (87 g) and extracted with a mixture of toluene and tetrahydrofuran. The resulting organic phase was concentrated under reduced pressure, and then the residue was stirred under heat at 170° C. for 6 hours in a nitrogen atmosphere. This reaction mixture was diluted with tetrahydrofuran, washed with an aqueous saturated sodium chloride solution, dried over magnesium sulfate, and concentrated under reduced pressure. The concentrate thus obtained was distilled under reduced pressure (bp 130 to 140° C./2 mmHg) to obtain 3,5-dimethyldodecanoic acid (5) (18.9 g, 0.0828 mol). A total yield of three steps from the 2-methylnonyl chloride (1Cl) was 67%.

IR (D-ATR): ν=2958, 2925, 2854, 1708, 1463, 1411, 1380, 1295 cm$^{-1}$.

$^1$H-NMR (500 MHz, CDCl$_3$): δ=0.84-0.89 (6H, m), 0.92-0.97 (3H, m), 1.00-1.17 (2H, m), 1.23-1.34 (12H, m), 1.43-1.50 (1H, m), 2.03-2.18 (2H, m), 2.28-2.40 (1H, m) ppm.

$^{13}$C-NMR (125 MHz, CDCl$_3$): δ=14.10, 19.27, 19.37, 20.02, 20.29, 22.68, 26.82, 27.00, 27.63, 27.68, 29.37, 29.91, 29.93, 30.00, 31.90, 36.62, 37.68, 41.47, 42.40, 44.30, 44.55, 179.87, 180.00 ppm.

GC conditions: Column: DB-WAX, (product of J&W Scientific) 30 m×0.25 mmφ, Temp: increased from 100° C. to maximum of 230° C. at 10° C./min, Injection temperature: 230° C., Carrier: He 1 ml/min, Split ratio: 100:1, Detector: FID, retention time: 13.812 min (syn-form) and 13.925 min (anti-form).

Example 2-2

Production of 3,5-dimethyldodecanoic acid (5)

(Hydrolysis in the Presence of Base, Followed by Addition of Acid and Decarboxylation)

In a nitrogen atmosphere, ethyl 2-(1,3-dimethyldecyl)malonate (4Et) (35.2 g, 0.107 mol) and a 13% by weight aqueous sodium hydroxide solution (104 g) were placed in a reaction vessel and stirred under refluxing with heating for one hour. Then, the resulting ethanol therein was distilled off in one hour. A 56% by weight aqueous sulfuric acid solution (93 g) was added thereto and the resulting mixture was under refluxing with heating for 30 hours. The reaction mixture was diluted with tetrahydrofuran. The organic phase was washed three times with an aqueous saturated sodium chloride solution and concentrated under reduced pressure. The concentrate thus obtained was distilled under reduced pressure (bp: from 130 to 140° C./2 mmHg) to obtain 3,5-dimethyldodecanoic acid (5) (21.6 g, 0.0944 mol). A total yield of three steps from the 2-methylnonyl chloride (1Cl) was 59%.

Example 2-3

Production of 3,5-dimethyldodecanoic acid (5)

(Hydrolysis Under Acidic Conditions, and Decarboxylation)

In a nitrogen atmosphere, ethyl 2-(1,3-dimethyldecyl)malonate (4Et) (18.6 g, 0.0566 mol), acetic acid (40 g), water (20 g), and sulfuric acid (2 g) were placed in a reaction vessel and stirred for 48 hours under refluxing with heating while distilling off ethanol. The reaction mixture was diluted with tetrahydrofuran and water. The organic phase was washed with an aqueous saturated sodium chloride solution and concentrated under reduced pressure. The concentrate thus obtained was distilled under reduced pressure (bp: from 130° C. to 140° C./2 mmHg) to obtain 3,5-dimethyldodecanoic acid (5) (11.4 g, 0.0498 mol). A total yield of three steps from the 2-methylnonyl chloride (1Cl) was 59%.

Example 3-1

Production of ethyl 3,5-dimethyldodecanoate (7)

<Krapcho Method>

In a nitrogen atmosphere, ethyl 2-(1,3-dimethyldecyl)malonate (4Et) (1.84 g, 0.00559 mol), sodium chloride (0.50 g, 0.0084 mol), water (0.60 g, 0.034 mol) and dimethylsulfoxide (20 ml) were placed in a reaction vessel and stirred at 170° C. for 8 hours. Then, water was added thereto, followed by extraction with hexane. The organic phase thus obtained was washed with water, dried over magnesium sulfate, and concentrated under reduced pressure to obtain a crude product (1.35 g, 0.0500 mol) of ethyl 3,5-dimethyldodecanoate (7Et).

A total yield of two steps from the 2-methylnonyl chloride (1 Cl) was 60%. The product was provided for the subsequent reaction as it was.

IR (D-ATR): ν=2957, 2925, 2872, 2854, 1738, 1463, 1378, 1176, 1034 cm$^{-1}$.

$^1$H-NMR (500 MHz, CDCl$_3$): δ=0.83-0.92 (9H, m), 0.93-1.36 (17H, m), 1.40-1.46 (1H, m), 1.98-2.19 (2H, m), 2.20-2.33 (1H, m), 4.09-4.14 (2H, m)

Example 3-2

Production of 3,5-dimethyldodecanoic acid (5)

(Hydrolysis of Ester)

In a nitrogen atmosphere, the crude product (1.22 g, 0.00452 mol) of ethyl 3,5-dimethyldodecanoate (7Et) produced in the method of Example 3-1, methanol (1 ml), a 25% by weight aqueous sodium hydroxide solution (3 ml) were placed in a reaction vessel and stirred at 65° C. for 2 hours. After addition of water, the resulting mixture was washed with a hexane-tetrahydrofuran mixture. The aqueous phase was made acidic in addition of 20% by weight hydrochloric acid, followed by extraction with a hexane-tetrahydrofuran mixture. The organic phase thus obtained was dried over magnesium sulfate and then concentrated under reduced pressure. The concentrate thus obtained was distilled under reduced pressure (bp: from 130 to 140° C./2 mmHg) to obtain 3,5-dimethyldodecanoic acid (5) (1.03 g, 0.00452 mol). A total yield of the three steps from the 2-methylnonyl chloride (1 Cl) was 60%.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. A method for producing 3,5-dimethyldodecanoic acid comprising the steps of:
converting 2-methylnonyl halide (1):

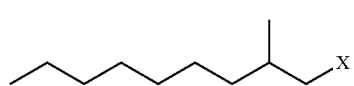

(1)

wherein X represents a halogen atom,
to a 2-methylnonyl metal reagent (2):

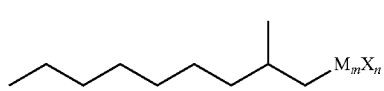

(2)

wherein M represents a monovalent or divalent metal, m stands for 1 or 0.5, and when m stands for 1, n stands for 0 or 1, and when m stands for 0.5, n stands for 0,
reacting the 2-methylnonyl metal reagent (2) with 2-ethylidene malonic acid ester (3):

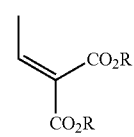

(3)

wherein Rs may be the same or different and each represents a monovalent hydrocarbon group having from 1 to 5 carbon atoms,
to form 2-(1,3-dimethyldecyl)malonic acid ester (4):

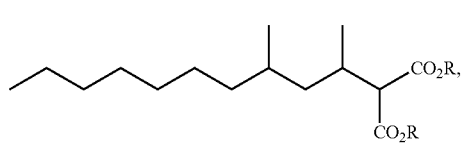

(4)

as a result of 1,4-addition of the 2-methylnonyl metal reagent (2) to the 2-ethylidene malonic acid ester (3), and
subjecting the 2-(1,3-dimethyldecyl)malonic acid ester (4) to decarboxylation or dealkoxycarbonylation to obtain 3,5-dimethyldodecanoic acid (5):

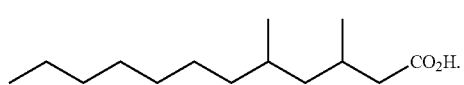

(5)

2. The method for producing 3,5-dimethyldodecanoic acid according to claim 1, wherein the step of subjecting the 2-(1,3-dimethyldecyl)malonic acid ester (4) to decarboxylation or dealkoxycarbonylation comprises:
hydrolyzing the 2-(1,3-dimethyldecyl)malonic acid ester (4) into 2-(1,3-dimethyldecyl)malonic acid (6):

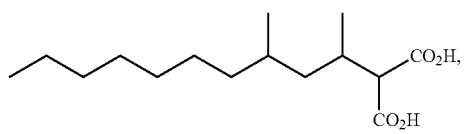

(6)

and
subjecting the 2-(1,3-dimethyldecyl)malonic acid (6) to decarboxylation to obtain the 3,5-dimethyldodecanoic acid (5).

3. The method for producing 3,5-dimethyldodecanoic acid according to claim 1, the step of subjecting the 2-(1,3-dimethyldecyl)malonic acid ester (4) to decarboxylation or dealkoxycarbonylation comprises:
subjecting the 2-(1,3-dimethyldecyl)malonic acid ester (4) to dealkoxycarbonylation to obtain 3,5-dimethyldodecanoic acid ester (7):

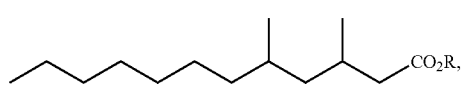

(7)

and hydrolyzing the 3,5-dimethyldodecanoic acid ester (7) into the 3,5-dimethyldodecanoic acid (5).

* * * * *